US008921826B2

(12) United States Patent
Hayat et al.

(10) Patent No.: US 8,921,826 B2
(45) Date of Patent: Dec. 30, 2014

(54) LIGHT SOURCE BASED ON SIMULTANEOUS TWO-PHOTON EMISSION

(75) Inventors: Alex Hayat, Carmiel (IL); Pavel Ginzburg, Rechovot (IL); Meir Orenstein, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

(21) Appl. No.: 11/987,071

(22) Filed: Nov. 27, 2007

(65) Prior Publication Data

US 2009/0135870 A1    May 28, 2009

(51) Int. Cl.
| H01L 33/00 | (2010.01) |
| H01S 5/183 | (2006.01) |
| B82Y 20/00 | (2011.01) |
| H04L 9/08 | (2006.01) |
| G02F 1/35 | (2006.01) |
| H01S 5/10 | (2006.01) |
| H01S 5/04 | (2006.01) |
| H01S 5/024 | (2006.01) |
| H01S 5/34 | (2006.01) |

(52) U.S. Cl.
CPC .............. *H01S 5/183* (2013.01); *H01S 5/105* (2013.01); *H01S 5/041* (2013.01); B82Y 20/00 (2013.01); *H04L 9/0852* (2013.01); *H01S 5/02415* (2013.01); *G02F 1/3526* (2013.01); *H01S 5/3412* (2013.01); *H01S 5/024* (2013.01); *A61B 2562/028* (2013.01)
USPC ................... 257/13; 257/E33.069; 257/98

(58) Field of Classification Search
CPC ....................................................... H01L 33/105
USPC ........................................................... 257/13
See application file for complete search history.

(56) References Cited

U.S. PATENT DOCUMENTS

| 5,034,613 | A | 7/1991 | Denk et al. |
| 5,684,621 | A | 11/1997 | Downing |
| 5,796,477 | A | 8/1998 | Teich et al. |
| 5,912,257 | A | 6/1999 | Prasad et al. |
| 5,957,960 | A | 9/1999 | Chen et al. |
| 6,020,591 | A | 2/2000 | Harter et al. |
| 6,267,913 | B1 | 7/2001 | Marder et al. |
| 6,396,617 | B1 * | 5/2002 | Scalora ......................... 359/248 |
| 6,605,822 | B1 | 8/2003 | Blais et al. |
| 6,674,778 | B1 * | 1/2004 | Lin et al. .................... 372/46.01 |
| 2002/0163947 | A1 * | 11/2002 | Ostergaard et al. ............. 372/43 |

OTHER PUBLICATIONS

Ironside, IEEE J.Q.E. vol. 28, No. 4, Apr. 1992 "Two-photon gain semiconductor amplifier" pp. 842-847.*
Marti et al., IEEE J.Q.E. vol. 39, No. 9, Sep. 2003, pp. 1066-1073, "Feasability . . . microcavity".*
Gauthier et al. "Realization of a Continuous-Wave, Two-Photon Optical Laser", Physical Review Letters, 68(4): 464-467, Jan. 27, 1992.
Goodwins Toshiba Claims Entangled Photon Breakthrough, ZDNet News on Jan. 11, 2006, CNET Networks, 2007.
Akopian et al. "Entangled Photon Pairs From Semiconductor Quantum Dots", Physical Review Letters, 96: 130501-1-130501-4, 2006.

(Continued)

*Primary Examiner* — Jerome Jackson, Jr.

(57) ABSTRACT

A semiconductor device which produces at least 1 W/m2 two photon emission power per area, when operating at one or more temperatures greater than 20 K.

28 Claims, 9 Drawing Sheets

(56) References Cited

OTHER PUBLICATIONS

Aspect et al. "Experimental Tests of Realistic Local Theories Via Bell's Theorem", Physical Review Letters, 47(7): 460-463, Aug. 17, 1981.

Bennett et al. "Communication Via One- and Two-Particle Operators on Einstein-Podolsky-Rosen States", Physical Review Letters, 69(20): 2881-2884, Nov. 16, 1992.

Clauser et al. "Proposed Experiment to Test Local Hidden-Variable Theories", Physical Review Letters, 23(15): 880-884, Oct. 13, 1969.

Hayat et al. "High-Rate Entanglement Source Via Two-Photon Emission From Emiconductor Quantum Wells", Physical Review B, 76(3): 035339-1-035339-4, 2007.

Hayat et al. "Two-Photon Emission From Semiconductors", ArXiv E-Print Service, p. 1-15, Oct. 25, 2007.

Heatley et al. "Ultrashort-Pulse Generation Using Two-Photon Gain", Optics Letters, 18(8): 628-630, Apr. 15, 1993.

Hutchings et al. "Nondegenerate Two-Photon Absorption in Zinc Blende Semiconductors", Journal of the Optical Society of America B, 9(11): 2065-2074, Nov. 1992.

Kumar et al. "Photonic Technologies for Quantum Information Processing", Quantum Information Processing, 3(1-5): 215-231, Oct. 2004.

Kwiat et al. "New High-Intensity Source of Polarization-Entangled Photon Pairs", Physical Review Letters, 75(24): 4337-4342, Dec. 11, 1995.

Lee et al. "Two-Photon Absorption With Exciton Effect for Degenerate Valence Bands", Physical Reviews B, 9(8): 3502-3516, Apr. 15, 1974.

Lemonias et al. "Carbon P+ Doping of Molecular-Beam Epitaxial GaAs Films Using Carbon Tetrabromide", Journal of Vacuum Science & Technology, B: Microelectronics and Nanometer Structures, 12(2): 1190-1192, Mar./Apr. 1994.

Li et al. "Optical-Fiber Source of Polarization-Entangled Photons in the 1550 NM Telecom Band", Physical Review Letters, 94: 053601-1-053601-4, 2005.

Nathan et al. "Review of Multiphoton Absorption in Crystalline Solids", Journal of the Optical Society of America B, 2(2): 294-316, Feb. 1985.

Nikolaus et al. "Two-Photon Laser", Physical Review Letters, 47(3): 171-173, Jul. 20, 1981.

Ning "Two-Photon Lasers Based on Intersubband Transitions in Semiconductor Quantum Wells", Physical Review Letters, 93(18): 187401-1-187403-4, Oct. 29, 2004.

Pelton et al. "Bright, Single-Spatial-Mode Source of Frequency Non-Degenerate, Polarization-Entangled Photon Pairs Using Periodically Poled KTP", Optics Express, 12(15): 3573-3580, Jul. 26, 2004.

Saleh et al. "Entangled-Photon Virtual-State Spectroscopy", Physical Review Letters, 80(16): 3483-3486, Apr. 20, 1998.

Sheik-Bahae et al. "Dispersion of Bound Electronic Nonlinear Refraction in Solids", IEEE Journal of Quantum Electronics, 27(6): 1296-1309, Jun. 1991.

Walton et al. "One-Way Entangled-Photon Autocompensating Quantum Cryptography", Physical Review A, 67: 062309-1-062309-4, 2003.

\* cited by examiner

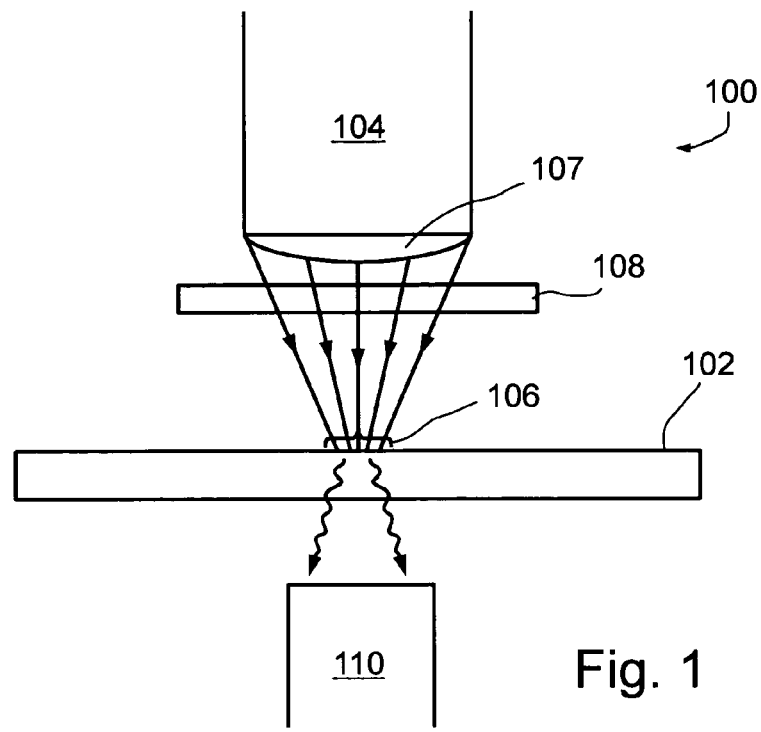
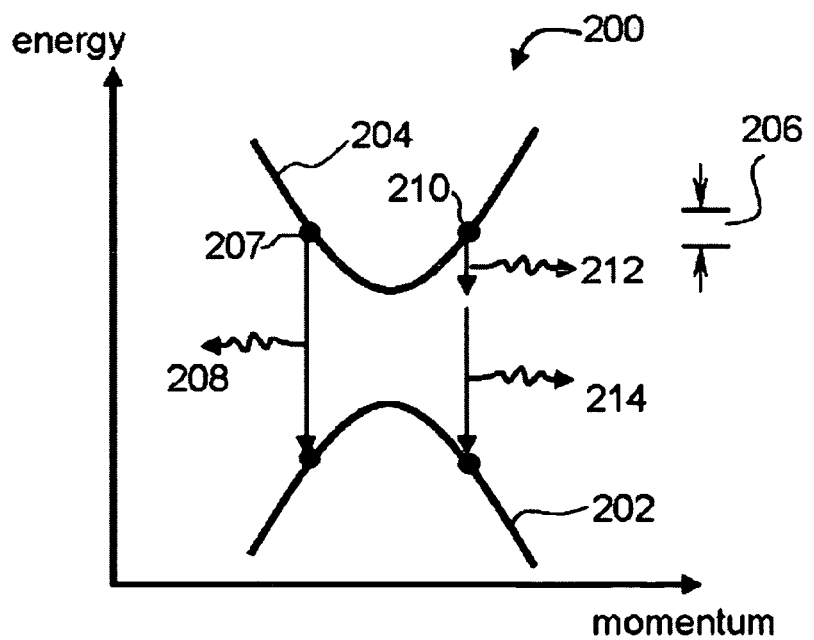

LIGHT SOURCE BASED ON SIMULTANEOUS TWO-PHOTON EMISSION

FIELD AND BACKGROUND OF THE INVENTION

The present invention, in some embodiments thereof, relates to photon pair generation and its applications.

Quantum entangled photon pairs can be used for quantum information processing, including quantum cryptography, quantum computing and quantum teleportation, as described, for example, by C. Bennett and S. J. Weisner, Phys. Rev. Lett. 69, 2881 (1992); P. Kumar et al, Quantum Inf. Process. 3, 215 (2004); Z. D. Walton et al, Phys. Rev. A, 67, 062309 (2003); and J. F. Clauser et al, Phys. Rev. Lett. 23, 880 (1969). Quantum entangled photon pairs can also be used for very low noise spectroscopy (including in vivo spectroscopy) and microscopy, as described, for example, by Saleh et al., Phys. Rev. Lett. 80, 3483 (1998) and by U.S. Pat. No. 5,796,477 to Teich et al.

Pairs of quantum entangled photons can be produced by using two photon emission from certain atomic radiative cascades, as described, for example, by A. Aspect, P. Gragnier and G. Roger, Phys. Rev. Lett. 47, 460 (1981), but these sources suffer from low brightness and polarization degradation caused by the atomic recoil.

Solid state sources of entangled photon pairs, based on parametric down conversion (PDC) of pump photons, for example in non-centrosymmetric crystals with second-order optical nonlinearity, have higher emission rates, and are described, for example, by P. G. Kwiat et al, Phys. Rev. Lett. 75, 4337 (1995), by M. Pelton et al, Opt. Express 12, 3573 (2004), and by X. Li et al, Phys. Rev. Lett. 94, 053601 (2005). But these sources have relatively low efficiency because they use post-selection or spatial filtering, and are based on a third-order (in the fine structure constant $\alpha$) non-resonant process in the time-dependent perturbation theory. PDC sources typically require pump lasers of high power, are bulky, and use exotic materials. The pump lasers typically used cost over $100,000.

Semiconductor quantum dots can also produce pairs of entangled photons, by single photon emission from pairs of entangled electrons, as described for example by N. Akopian et al, Phys. Rev. Lett. 96, 130501 (2006), and they are more efficient than PDC sources. However, quantum dot sources have low generation rates, their emission wavelengths are not tunable, currently only optical excitation is implemented and they require cryogenic temperatures, typically lower than 20 K. An article by Rupert Goodwins, dated Jan. 11, 2006 and downloaded from the internet at http://news.zdnet.com/2100-1009_22-6026098.html, on Nov. 18, 2007, quotes Andrew Shields, head of the Quantum Information group at Toshiba Research Europe, as saying that there is no reason in principle why quantum dots could not produce entangled pairs of photons at room temperature, but states that there are still challenges to be overcome before achieving such a device.

Two-photon amplifiers and lasers are described, for example, by C. N. Ironside, IEEE J. of Quantum Elect. 28, 842 (1992); C. Z. Ning, Phys. Rev. Lett. 93, 187403 (2004); D. H. Marti et al, IEEE J. of Quantum Elect. 39, 1066 (2003); and D. R. Heatley et al, Opt. Lett. 18, 628 (1993). Heatley et al describe using two-photon amplifiers and for pulse generation, because the gain in two-photon lasers/amplifiers, in contrast to conventional single photon lasers, is nonlinear, depending on the amplitude of the light wave.

Two photon absorption in semiconductors has been investigated, for example, by V. Nathan et al, J. Opt. Soc. Am. B 2, 294 (1985); C. C. Lee and H. Y. Fan, Phys. Rev. B 9, 3502 (1974); N. G. Basov et al, J. Phys. Soc. Japan Suppl. 21, 277 (1966); D. C. Hutchings and E. W. Van Stryland, J. Opt. Soc. Am. B 9, 2065 (1992); and M. Sheik-Bahae et al, IEEE J. Quantum Electron. 27, 1296 (1991).

The disclosures of the above mentioned documents are incorporated herein by reference.

SUMMARY OF THE INVENTION

An aspect of some embodiments of the invention relates to a semiconductor device, which produces more than 1 W/m$^2$ of two photon emission power, or more than 3 W/m$^2$, or more than 10 W/m$^2$, or more than 30 W/m$^2$, when operating at least one temperature above 20 K, or above 50 K, or above 100 K, or above 200 K, for example at room temperature. Optionally, the total two photon emission is more than 1 nW, or more than 3 nW, or more than 10 nW, or more than 30 nW, or more than 100 nW. In some embodiments of the invention, the two photon emission predominantly comprises quantum entangled photon pairs, each pair uncorrelated with other pairs. In some other embodiments of the invention, generally with higher power two photon emission, the two photon emission predominantly comprises two photon laser and/or amplifier emission.

Semiconductor sources of entangled photon pairs using two photon emission are more efficient than PDC sources of entangled photon pairs, in part because the emission rate is proportional to the square of the fine structure constant, $\alpha$, rather than being proportional to the cube of $\alpha$, as in PDC sources. As a result, there is no need for very high power expensive pump lasers to drive the semiconductor sources, and the device can be much less expensive than a PDC source. In some embodiments of the invention, electric power is used for pumping the semiconductor source, rather than using a laser for pumping, and this possibility is another potential advantage of semiconductor sources over PDC sources. Electrically pumped devices can be much smaller and less expensive than optically pumped devices.

Operating at or above room temperature, or even at relatively high cryogenic temperatures, makes these semiconductor two photon emission sources much more practical, for many applications, than quantum dot sources of entangled photon pairs, which generally operate at low cryogenic temperatures, for example 20K or less.

The two photon emission devices differ from quantum dot sources, in that pairs of entangled photons are produced by two photon emission from one electron, rather than by one photon emission per electron from a pair of entangled electrons, as is done in quantum dot sources.

An aspect of some embodiments of the invention relates to a semiconductor device which emits light with a broad continuous energy spectrum, from two photon emission, within a continuous range of photon energies.

The energy spectrum is sufficiently broad so that no more than half the power emitted within this range is emitted within any sub-range of the range that is narrower than 15% of the mean photon energy within the range, or narrower than 20% of the mean photon energy, or narrower than 30% of the mean photon energy, or narrower than 0.3 eV. Having such a broad spectrum may allow the source to be used for applications, such as spectroscopy, that cannot benefit from single photon semiconductor sources, such as LEDs, which have a narrower emission spectrum. Optionally, the device emits light with such a broad spectrum at least one temperature above 20 K, or above 50 K, or above 100 K, or above 200 K, for example at room temperature.

An aspect of some embodiments of the invention relates to a semiconductor device which non-thermally emits light of wavelength greater than 2 μm, with power per area greater than 1 W/m², or greater than 3 W/m², or greater than 10 W/m², or greater than 30 W/m².

Optionally, the light emitted at wavelength greater than 2 μm is predominantly between 2 μm and 4 μm. Optionally, the light at wavelengths above 2 μm is from two photon emission. There may also be substantial single photon emission at shorter wavelengths, for example about 1.5 μm, but this emission may be filtered out. The longest wavelength light produced by known single photon direct band wide-spectrum interband semiconductor light sources, such as the indium phosphide-type LED sources used for telecommunications, is typically about 1.3 to 1.5 μm. Two photon emission from the same material produces a broad spectrum centered at about twice that wavelength, for example between 2.5 and 3 μm, and extending up to 4 μm or beyond.

Optionally, the light has a continuous energy spectrum sufficiently broad so that there is no continuous sub-range of photon energies that is narrower than 15% of the mean emitted photon energy, and includes more than 50% of the emitted power. Optionally, there is no such sub-range that is narrower than 20% of the mean photon energy, or narrower than 30% of the mean photon energy, or narrower than 0.1 eV. Optionally, but not obligatorily, there is no continuous sub-range of photon energies, with wavelength longer than 2 μm, that includes more than 50% of the power emitted at wavelengths longer than 2 μm and is narrower than 15%, more preferably 20%, more preferably 30% of the mean photon energy emitted at wavelength greater than 2 μm, or narrower than 0.1 eV.

Optionally, the device produces light of these wavelengths when operating at least one temperature above 20 K, or above 50 K, or above 100 K, or above 200 K.

An aspect of some embodiments of the invention concerns a semiconductor two-photon optical amplifier or laser. The energy spectrum characterizing the optical amplifier or laser is sufficiently broad so that no more than half the power emitted within this range is emitted within any sub-range of the range that is narrower than 15% of the mean photon energy within the range, or narrower than 20% of the mean photon energy, or narrower than 30% of the mean photon energy, or narrower than 0.3 eV.

Optionally, the two photon optical amplifier or laser operates at low input peak powers. In various exemplary embodiments of the invention the two photon optical amplifier or laser operates at input peak power of less than 1000 W, more preferably less than 500 W, more preferably less than 250 W, more preferably less than 100 W, more preferably less than 50 W, more preferably less than 10 W, more preferably less than 1 W.

Optionally, the two photon optical amplifier or laser is used to produce short pulses, taking advantage of the nonlinear gain of two photon lasers. Optionally, more than half the energy of each pulse is emitted in a time shorter than X times the wave period for the mean emission frequency and the peak power of each pulse is greater than twice the time average power, where X equals 50, more preferably 40, more preferably 30, more preferably 20, more preferably 10, more preferably 5, more preferably 3.

The broad emission spectrum of a two photon laser may be especially useful for generating very short pulses, because the pulse length is inversely proportion to the bandwidth of the emission spectrum.

Optionally, for any of these devices, the semiconductor is a direct band semiconductor. Optionally, the device comprises a heterostructure, which allows injected electrons to be trapped long enough to fall from the conduction band to the valence band, making electrical pumping possible. Optionally, the device is electrically pumped. Alternatively, with or without a heterostructure, the device is optically pumped. Optionally, the heterostructure comprises a quantum well. Using a quantum well has the potential advantage that the conduction band is divided into several energy bands, each of which has a lower thermal energy spread than the conduction band in a uniform semiconductor. Optionally, the energy efficiency of the device is greater than $1 \times 10^{-9}$.

Optionally the device produces a total emission power, or a total two-photon emission power, greater than 3 nW, or 10 nW, or 30 nW, or 100 nW. Optionally, the device comprises anti-reflection coatings to raise the lasing threshold to greater than $10^8$ A/m², or greater than $2 \times 10^8$ A/m², or greater than $3 \times 10^8$ A/m².

An aspect of some embodiments of the invention concerns a method of designing a semiconductor device that produces two photon emission, the method comprising using a dephasing factor in calculating the two photon emission spectrum. Optionally, the device comprises an optical cavity, which may comprise a photonic structure. Optionally, obtaining an accurate calculation of the two photon emission spectrum for a given design of the photonic structure depends on using the dephasing factor.

According to an aspect of some embodiments of the present invention there is provided a semiconductor device which produces at least 1 W/m² two photon emission power per area, when operating at least one temperature greater than 20 K.

According to some embodiments of the invention the two photon emission power per area is at least 3 W/m².

According to some embodiments of the invention the two photon emission power per area is at least 10 W/m².

According to some embodiments of the invention the two photon emission power per area is at least 30 W/m².

According to some embodiments of the invention the device produces a two photon emission power of at least 1 nW.

According to some embodiments of the invention the device produces a two photon emission power of at least 3 nW.

According to some embodiments of the invention the device produces a two photon emission power of at least 10 nW.

According to some embodiments of the invention the device produces a two photon emission power of at least 30 nW.

According to some embodiments of the invention the temperature(s) is greater than 50 K.

According to some embodiments of the invention the temperature(s) is greater than 100 K.

According to some embodiments of the invention the temperature(s) is greater than 200 K.

According to some embodiments of the invention the two photon emission power per area quantum entangled photon pairs of at least 1 W/m².

According to some embodiments of the invention the device is electrically pumped.

According to some embodiments of the invention the device comprises a heterostructure.

According to some embodiments of the invention the heterostructure comprises a quantum well.

According to some embodiments of the invention the device is optically pumped.

According to some embodiments of the invention the energy efficiency of the device is greater than $1 \times 10^{-9}$.

According to some embodiments of the invention the device comprises an anti-reflection coating of sufficiently low reflectivity so that the lasing threshold is greater than $2\times10^8$ A/m$^2$.

According to an aspect of some embodiments of the present invention there is provided a semiconductor device which emits light with a broad continuous energy spectrum, from two photon emission, wherein the energy spectrum is sufficiently broad so that no more than half the power emitted within this range is emitted within any sub-range of the range that is narrower than 15% of the mean photon energy within the range.

According to some embodiments of the invention no more than half the power emitted within this range is emitted within any sub-range of the range that is narrower than 20% of the mean photon energy within the range.

According to some embodiments of the invention no more than half the power emitted within this range is emitted within any sub-range of the range that is narrower than 30% of the mean photon energy within the range.

According to some embodiments of the invention no more than half the power emitted within this range is emitted within any sub-range of the range that is narrower than 0.3 eV.

According to an aspect of some embodiments of the present invention there is provided a semiconductor device which non-thermally emits light of wavelength greater than 2 μm, with power per area greater than 1 W/m$^2$.

According to some embodiments of the invention at least 1 W/m$^2$ of the emitted light comes from two photon emission.

According to some embodiments of the invention the light has a continuous energy spectrum sufficiently broad so that there is no continuous sub-range of photon energies, with wavelength longer than 2 μm, that is narrower than 15% of the mean photon energy emitted at wavelength greater than 2 μm, and includes more than 50% of the power emitted at wavelengths above 2 μm.

According to an aspect of some embodiments of the present invention there is provided a semiconductor light emitting device, with energy spectrum sufficiently broad so that no more than half the power emitted within this range is emitted within any sub-range of the range that is narrower than 15% of the mean photon energy within the range.

According to some embodiments of the invention the device serves as an optical amplifier.

According to some embodiments of the invention the device serves as laser device and comprises an optical cavity for providing optical feedback for laser radiation.

According to some embodiments of the invention the device is operative at input peak power of less than 1000 W.

According to an aspect of some embodiments of the present invention there is provided a continuous wave laser device. The device comprises a semiconductor device configured for simultaneous emission of an idler photon and a signal photon; and a two-resonance optical cavity which provides a first resonance for the idler photon and a second resonance for the signal photon, wherein the first resonance is of higher quality factor than the second resonance.

According to an aspect of some embodiments of the present invention there is provided a system for analyzing a material. The system comprises a semiconductor device configured for simultaneous emission of an idler photon and a signal photon; a photon detector characterized by a detection threshold which equals the sum of energies of the signal and idler photon; wherein an optical path for the signal photon is defined from the semiconductor device through the material to the detector, and an optical path for the idler photon is defined from the semiconductor device to the detector while bypassing the material.

According to an aspect of some embodiments of the present invention there is provided a method of designing a semiconductor device for two photon emission, the method comprising: (a) choosing a desired range of values for each of one or more emission characteristics for the two photon emission for the device; (b) choosing a tentative design of the device; (c) calculating values of the emission characteristics for a device of the tentative design, using a dephasing factor; (d) comparing the at least one desired ranges with the at least one calculated values; (e) adjusting the tentative design if the at least one calculated values are not within their respective desired ranges; and (f) if the calculated values are not within their respective desired ranges, repeating (c), (d) and (e) at least once, using the adjusted design.

According to some embodiments of the invention the tentative design comprises an optical cavity, and the at least one calculated emission characteristics depends on an emission spectrum which depends on dimensions of the optical cavity and on the dephasing factor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 schematically shows a cross-sectional view of a bulk semiconductor device for optically pumped two photon emission, according to an exemplary embodiment of the invention;

FIG. 2 schematically shows a diagram of the energy bands and the two photon emission process in a bulk semiconductor, such as the semiconductor used in the device of FIG. 1;

DESCRIPTION OF EMBODIMENTS OF THE INVENTION

Figure 3:
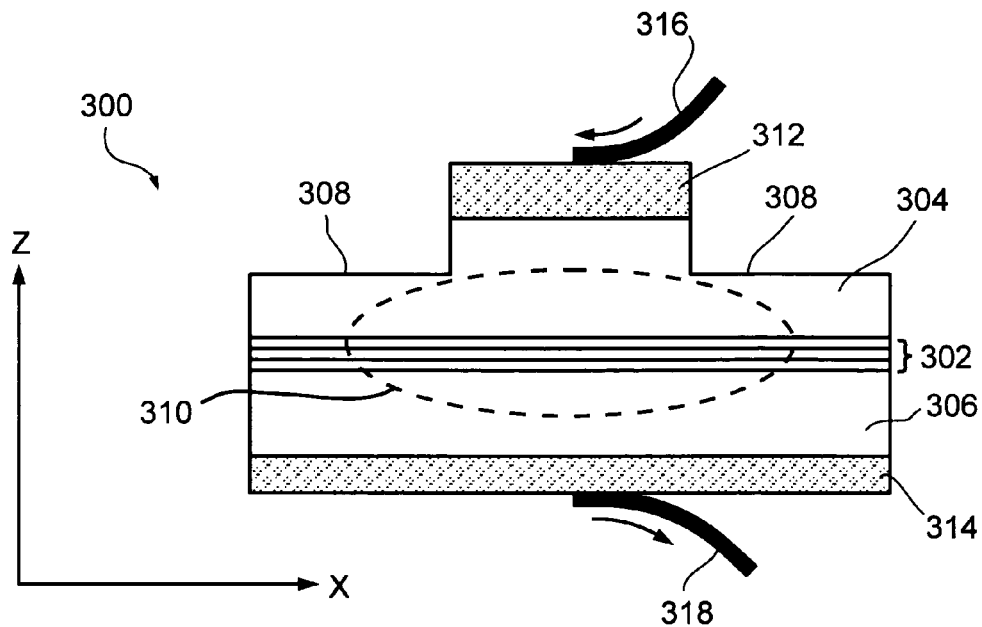
FIG. 3 schematically shows a cross-sectional view of a semiconductor device with quantum wells, for electrically driven two photon emission, according to an exemplary embodiment of the invention.

The present invention, in some embodiments thereof, relates to photon pair generation and its applications.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

An aspect of some embodiments of the invention relates to a semiconductor device, which produces light by two-photon emission. The device of the present embodiments is operative at sufficiently high temperatures, and is typically capable of providing sufficiently high two photon emission power. In various exemplary embodiments of the invention the device is operative at temperatures which are higher than 20 K, more preferably higher than 50 K and more preferably higher than 100 K. In some embodiments, the device is operative at non-cryogenic temperatures, e.g., at room temperature (about 300 K).

Operating at the above temperatures, particularly, but not exclusively, at non-cryogenic temperatures, makes the semiconductor two photon emission device of the present embodiments advantageous over traditional quantum dot sources of entangled photon pairs, which generally operate at low cryogenic temperatures, for example 20 K or less. The present inventors found that there are fundamental challenges for manufacturing quantum dot sources operating room temperature. This is because making such sources would require increasing the energy depth of the quantum dot (the difference in energy gaps between the materials forming the quantum dot) by two or more orders of magnitude. For example, conventional quantum dot sources are made of materials with a characteristic energy depth of order of tens of meV. However, photon pair emission from quantum dots can only be achieved at room temperature for a characteristic quantum dot energy depth of order of 1 eV, and semiconductors materials allowing such operation are GaN and ALN, which have very poor conductivity and are extremely difficult to fabricate with sufficient quality.

From the standpoint of emission mechanism, a quantum dot based photon pair device emits a single photon as a result of two electron-hole pairs recombination, while an electron-hole pair in the two-photon emission semiconductor device of the present embodiments can emit two photons. Thus, a photon pair emitted by a conventional quantum dot originates from two electron-hole bound pairs, while two photons emitted from the device of the present embodiments originate from a single electron-hole pair.

Referring now to the drawings, FIG. 1 schematically shows a cross-sectional view of an exemplary optically pumped device 100 for producing spontaneous two photon emission. Device 100 uses a sample 102 of a direct band semiconductor material, for example GaAs. A pump laser 104 with a photon energy above the band gap of semiconductor sample 102, for example a continuous wave 514 nm argon laser, chosen because it has photon energy greater than the band gap of semiconductor sample 102, is focused, e.g., by a focusing lens 107, onto a small spot 106, about 30 μm diameter for example, on the surface of sample 102, after passing through a filter 108 which filters out spontaneous parasitic infrared emission from laser 104.

When the pump laser has a power of 100 mW, it produces a local carrier density of electrons in the conduction band of about $1.2 \times 10^{18}$ cm$^{-3}$ in the sample adjacent to the spot, and induces about 3 nW of two photon emission, which is transmitted through the sample, and detected with a photoreceiver 110, for example a New-Focus infrared femtowatt photoreceiver with a lock-in amplifier. Making spot 106 smaller generally increases the power per area of the two photon emission, and makes it easier to detect. If the area of spot 106 is too small, it may be difficult to collect light from it, due to the numerical aperture of the light-collecting objective The signal to noise ratio is optionally improved by chopping the pump laser, for example at 236 Hz, and locking in the photoreceiver amplifier to the chopping rate of the laser. Although a higher power pump laser would produce a higher carrier density, for example 180 mW would produce a carrier density of $2 \times 10^{18}$ cm$^{-3}$ in the sample, and might produce higher two photon emission power, in device 100 the laser power may be limited by heating of the sample, which reaches 330 K when the laser power is 100 mW. If the spot gets too hot, for example much hotter than 330 K, then the non-radiative recombination rate of electrons and holes increases, significantly decreasing radiative recombination, including two photon emission.

Optionally, as described below for device 300 in FIG. 3, device 100 is cooled, for example by a thermoelectric cooler, allowing higher pump laser power to be used, and possibly higher two photon emission power to be achieved.

FIG. 2 is a schematic plot 200 of the energy of the valence band 202, and the energy of the conduction band 204, as a function of the electron crystal momentum. Because the semiconductor sample 102 is a direct band semiconductor, the minimum energy of the conduction band occurs at the same momentum as the maximum energy of the valence band, so an electron 207 in the conduction band 204 can recombine with a hole and fall directly to the valence band, emitting a single photon 208 with energy equal to the band gap, about 1.4 eV in the case of GaAs. In two photon emission, an electron 210 in the conduction band falls to the valence band by emitting two photons 212 and 214, the sum of whose energy is equal to the band gap, or slightly greater due to the thermal spread 206 of the energies of electrons of differing momentum in the conduction band. The rate of spontaneous two photon emission is proportional to the square of the fine structure constant $\alpha$.

Device 100, and experiments done with it, are described by the inventors Hayat et al in an article entitled "Two-Photon Emission from Semiconductors", published in the arXiv e-print service (hereinafter Hayat et al 0701114). The article was downloaded from the internet at http://www.arxiv.org/pdf/quant-ph/0701114v3 on Oct. 25, 2007, and the disclosure of which is incorporated herein by reference. This article states, at the end of the second paragraph, "Semiconductors can be injected with very high charge carrier densities, making even the weak second-order spontaneous processes measurable and their TPE spectrum is expected to be determined by the photonic state density as well as by the carrier energy distribution." Evidence that the observed emission is really two photon emission, and not inhomogeneously broadened one-photon emission involving mid-gap energy levels, is provided by the fact that stimulating the sample with a given photon energy, in the presence of the pump laser, produces stimulated emission at a photon energy equal to the band gap minus the stimulating photon energy, and suppresses two photon emission at other photon energies.

The semiconductor material used for sample 102 should preferably be a direct band material which is sufficiently pure and free of defects. Too many impurities and defects increase non-radiative recombination of electrons and holes, decreasing radiative recombination including two photon emission. Impurities and defects also produce mid-gap energy levels, leading to single photon emission lines at energies similar to the continuum two photon emission spectrum, potentially making it more difficult to detect and measure the two photon emission spectrum unless the emission lines can be filtered out. In addition to GaAs, for example, such materials include semiconductors with some or all of the Ga replaced by In and/or Al, and with some or all of the As replaced by P and/or Sb, for example InP, AlP, GaP, AlAs, InSb, InAs, and their various alloys. Although GaN is also a direct band semiconductor, and could in principle be used, in practice GaN may not yet be available in crystals that are sufficiently pure and defect-free. A potential advantage of using GaN for two photon emission, once sufficiently pure and defect-free crystals are available, is that the two photon emission would be mostly in the near infrared, and could be detected by Si detectors.

FIG. 3 schematically shows a side cross-sectional view of an electrically driven semiconductor device 300 for two photon emission, using quantum wells.

Device 300 is advantageous over PDC sources which are not electrically driven. The present inventors found that it is extremely difficult to produce electrically driven quantum dots sources, all the more so electrically driven quantum dots sources operating at sufficiently high (e.g., above 20K, more preferably non-cryogenic temperatures). Thus, device 300 is also advantageous over quantum dots two-photon sources.

The structural difference between a quantum well and a quantum dot is that in a quantum dot, there is a three-dimensional confinement of electron-hole bound pairs, while in a quantum well the electron-hole bound pairs are confined in one-dimension and are generally free in the other two-dimensions.

In various exemplary embodiments of the invention the quantum wells of device 300 are located in layer 302, and consist of four periods of compressively strained $Ga_{0.45}In_{0.55}P$, each about 5 nm thick, separated by barriers of $(Al_{0.5}Ga_{0.5})_{0.51}In_{0.49}P$, each about 5.5 nm thick. Layer 302 is surrounded on top and bottom by layers 304 and 306 of AlGaInP cladding, which provide structural integrity for layer 302.

The coordinate system in FIG. 3 is conveniently selected such that the layers are parallel to the x and y directions, and the z direction is along the growth direction of the layers.

Depressions 308 are etched into layer 304 on two sides, leaving a raised central ridge of about 4 μm wide. This configuration provides an effective lower index of refraction on the two sides, confining light emitted in layer 302 to a central region 310 of device 300. The emitted light is also confined vertically by the fact that the quantum well layer 302 has a higher index of refraction than cladding layers 304 and 306. As a result, the emitted light travels along the length of device 300, in a direction perpendicular to the plane of FIG. 3, and can be collected efficiently by photoreceivers located at one or both ends.

Optionally, a cap 312, on top of cladding layer 304, made of heavily doped GaAs, and a similar heavily doped GaAs substrate 314 below cladding layer 306, provide electrical contacts respectively for electrical leads 316 and 318. Optionally, one or both of the cap and substrate is coated with a thin layer of gold, to which the electrical leads are attached. Such heavily doped GaAs layers are often used as electrical contacts for semiconductor devices, because they do not oxidize as readily as a metal contact would. The $p^+$ doping is optionally done with carbon that can reach densities greater than $10^{19}$ $cm^{-3}$. This material is described, for example in Lemonias et al Journal of Vacuum Science & Technology B: Microelectronics and Nanometer Structures, March 1994, Volume 12, Issue 2, pp. 1190-1192. A thermoelectric cooler, in contact with the other side substrate 314, optionally maintains device 300 at a temperature of about 300° K.

Figure 4:
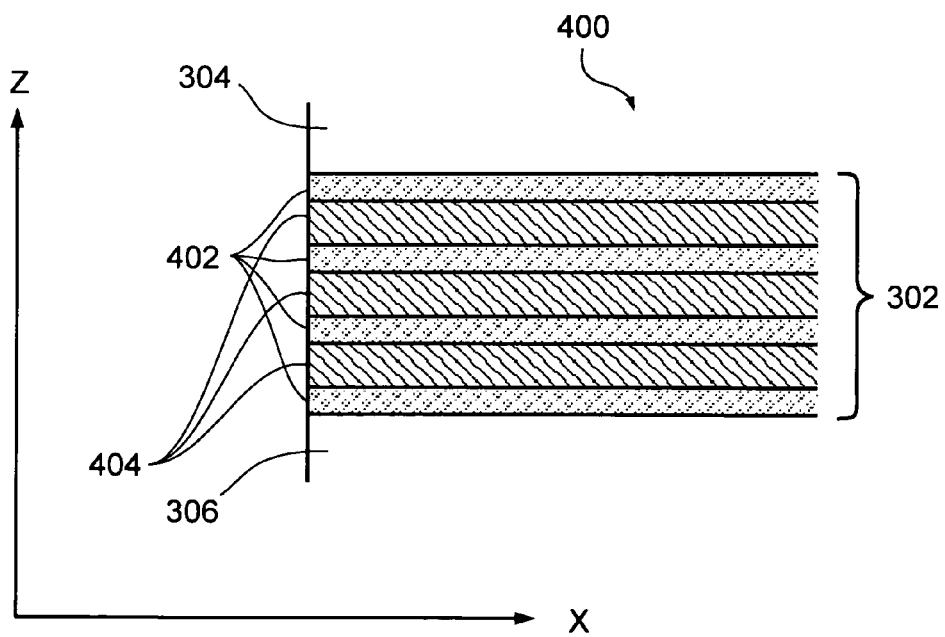
FIG. 4 schematically shows a more detailed view of the quantum wells in the device shown in FIG. 3.

FIG. 4 schematically shows a more detailed view of the quantum wells in layer 302. There are, for example, four wells 402, separated by barriers 404. The wells and the barriers have different effective electric potentials for the electrons in the conduction and valence bands, and/or different effective electron masses. As a result, the electrons have a discrete set of wave functions in the z-direction, and the z component of electron crystal momentum has certain discrete values. Such quantum well wave functions are illustrated, for example, for a single quantum well, in the textbook on diode lasers by Coldren and Corzine [L. A. Coldren and S. W. Corzine, "Diode Lasers and Photonic Integrated Circuits", Wiley, New York, 1995] in FIG. 4.4 on page 123. As a result, the electrons occupy discrete narrow energy sub-bands within the conduction band.

Figure 5:
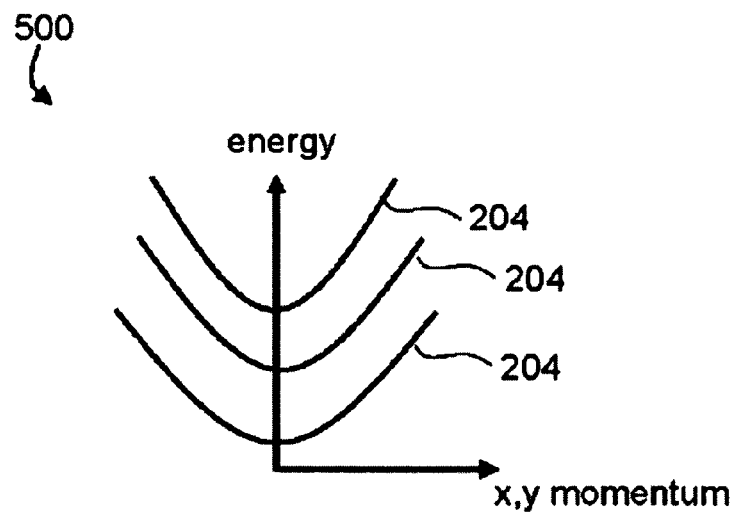
FIG. 5 schematically shows a diagram of the conduction energy bands of a semiconductor with quantum wells, such as that shown in FIG. 3.

Diagram 500 in FIG. 5 schematically shows energy sub-bands in conduction band 204, as a function of $k_x$ and $k_y$, the x and y components of the crystal momentum. For clarity of presentation, the valence band is not shown in FIG. 5 but one of ordinary skill in the art would know the shape of the valence band. The localization of the quantum wells along the z direction is typically defined to a high level of accuracy, thereby rendering high the uncertainty of $k_z$, the z component of the electron crystal momentum. The energy quantization due to the aforementioned z-localization determines the parameters (curvature, minima level, etc.) describing the energy sub-bands shown in FIG. 5.

The difference in minimum energy between adjacent sub-bands of the conduction layer is, for example, comparable to the electron thermal energy, or about 2 or 3 times less than the electron thermal energy. The discrete sub-bands may make the emission energy more sharply defined, and less sensitive to applied current and temperature. Quantum wells may also decrease the effective mass of holes, increasing their mobility, and decreasing the current needed for emission.

Experiments on two photon emission using device 300 are described in the paper by the inventors Hayat et al 0701114 supra. When 200 mA of current was injected through cap 312 in device 300, two photon emission of 30 nW was observed, together with a narrow band single photon emission at about 1.4 eV. The overall one-photon emission from the whole device was about 3 mW. The two photon emission was broadband, with a maximum at 0.98 eV, in good agreement with theoretical calculations described in the paper, and the two photon emission power was also in good agreement with theoretical calculations. Further evidence that this emission was really two photon emission is provided by experiments in which stimulating the device with a given photon energy, while driving it electrically, produced stimulated emission at the band gap energy minus the energy of the stimulating photons, similar to the experiment described above for optically pumped device 100. In addition, an experiment was done, driving device 300 with 10 ns pulses of current and measuring the correlation between the signal in two photoreceivers, which demonstrated that pairs of photons are emitted simultaneously, as expected for two photon emission.

Figure 6:
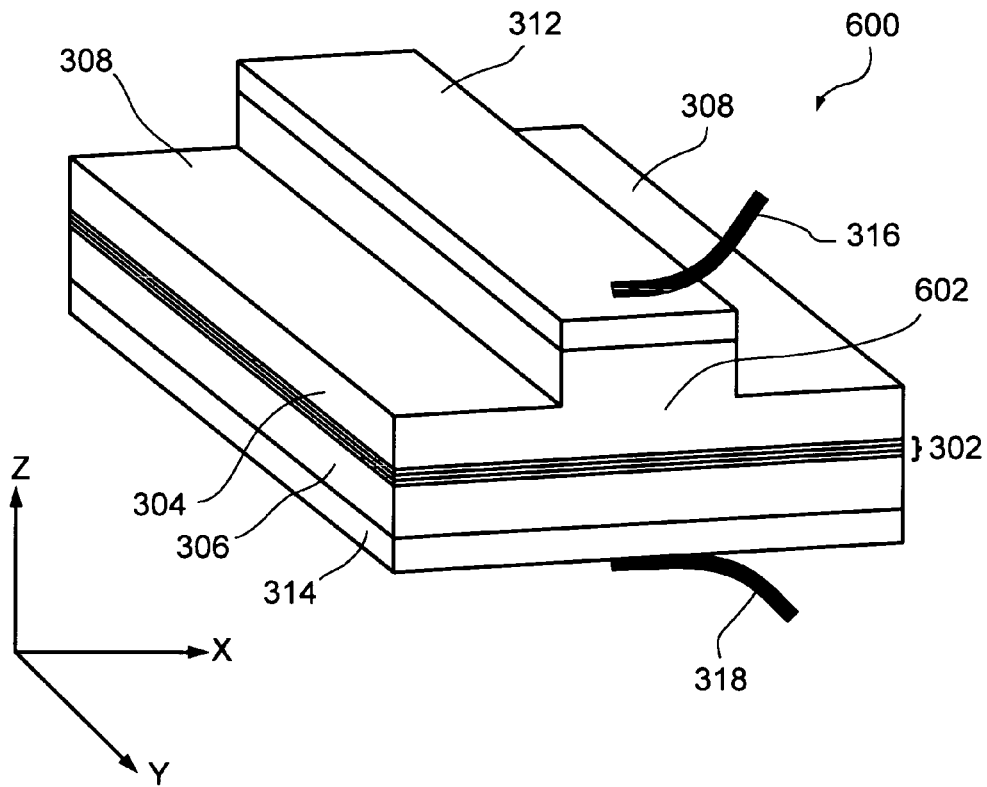
FIG. 6 schematically shows a perspective view of the device shown in FIG. 3, showing an anti-reflection coating.

FIG. 6 schematically shows a perspective view of device 300. Facets 602, at the ends of the device (one of them hidden from view in FIG. 6), are coated with an anti-reflection coating, to increase the threshold for single photon lasing above 200 mA. The carrier density, and hence the two photon emission power, does not increase with increasing current above the single photon laser threshold current, so increasing the laser threshold current allows higher two photon emission power to be achieved. Optionally, the device is run with current comparable to the lasing threshold, to maximize the two photon emission power. If the current is even slightly above the lasing threshold, there will generally be a high power of emitting single photon laser emission, but this light will generally be at a shorter wavelength than the two photon emission, and may be filtered out.

In some embodiments of the invention, the two photon emission power is enhanced, relative to the single photon emission power (whether above or below the laser threshold), by using an appropriately designed optical cavity, which only supports modes at the two photon emission wavelengths. For example, a paper by the inventors, A. Hayat, P. Ginzburg, M. Orenstein, "High-rate entanglement source via two-photon emission from semiconductor quantum wells", Phys. Rev. B, 76 035339, 2007 (hereinafter Hayat et al Phys. Rev. B) describes a semiconductor device for two photon emission, utilizing such an optical cavity. The disclosure of this article is incorporated herein by reference. This article, in the second column of the first page, describes using "two-photon emission (TPE) from quantum wells (QW) in a semiconductor photonic cavity," and states: "The QW structure is pumped electrically and a vertical doubly resonant microcavity is designed to preferentially select the two-photon transition wavelength modes: the signal $\omega_s$ and idler $\omega_i$, by methods used for GaAs-based nonlinear optics," referencing G. Klemens, C.-H. Chen and Y. Faiman, Opt. Express 13, 9388 (2005).

In some embodiments of the invention, although not in the design described in the Phys. Rev. B paper just referenced, the two photon emission spectrum is calculated using a dephasing factor $\Gamma$ determined, for example, by the carrier decoherence time, which may be less than 100 femtoseconds. Such a dephasing factor may be needed to prevent the calculated two-photon emission spectrum from diverging at low frequency, as can be seen in Eq. (3) of Hayat et al 0701114.

Figure 7:
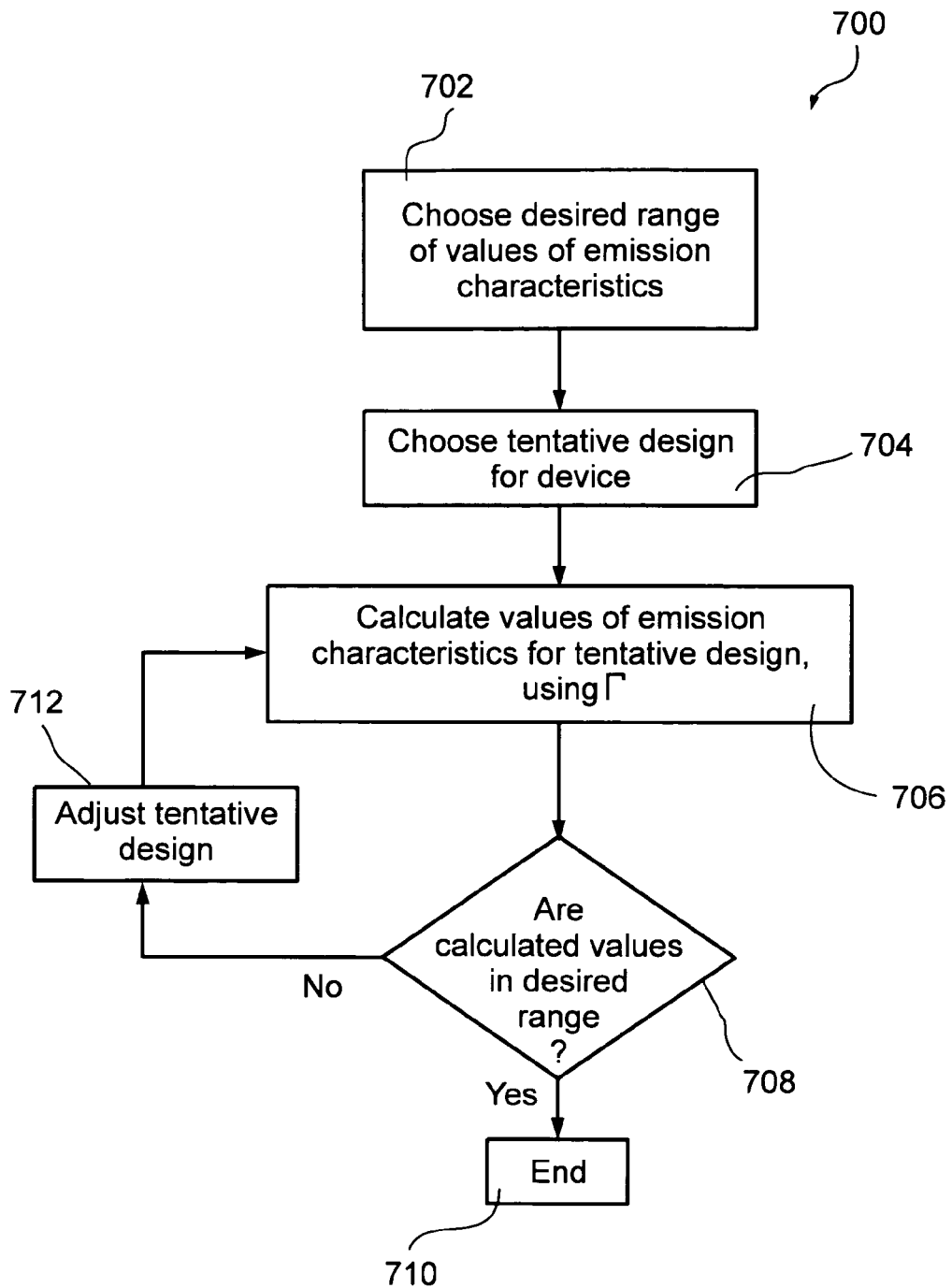
FIG. 7 shows a flowchart for a design method for semiconductor devices exhibiting two photon emission, according to an exemplary embodiment of the invention.

FIG. 7 shows a flowchart 700 for a method of designing semiconductor two photon emission devices, taking into account the dephasing factor. In 702, a desired range of values of one or more characteristics of the two photon emission spectrum is chosen. In 704, a tentative design is chosen for the device. Optionally the design includes a photonic structure such as an optical cavity. In 706, the values of the one or more characteristics are calculated, for example using Eqs. (2) and (3) of Hayat et al to find the two photon emission spectrum, taking into account the dephasing factor $\Gamma$. In 708, the calculated values are compared to the desired ranges of the values. If the calculated values are all in the desired ranges, then the design process ends at 710, and the tentative design becomes the final design. If the calculated values are not all in the desired ranges, then, at 712, the tentative design is adjusted, using, for example, any of the methods of negative feedback control known in the art, and values of the emission characteristics for the new design is calculated at 706. This process is continued, optionally until a design with the desired characteristics is found.

Figure 8:
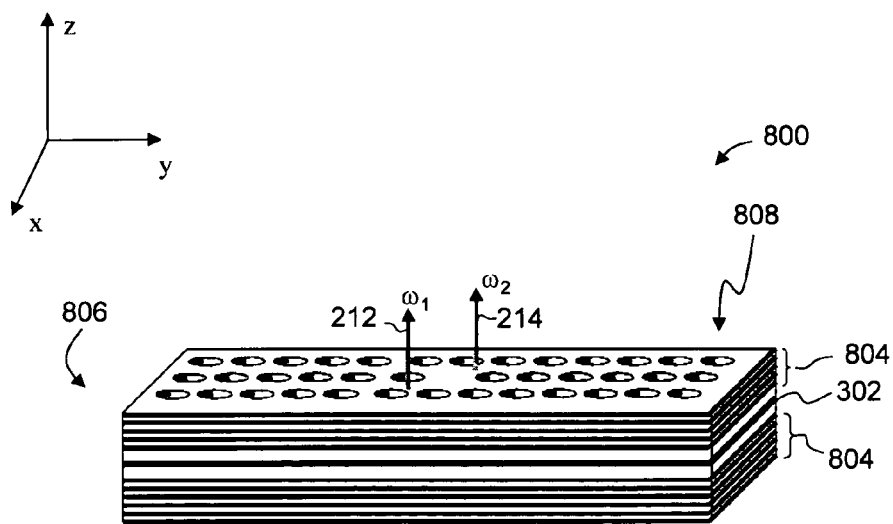
FIG. 8 schematically shows a cross-sectional view of a semiconductor device exhibiting two photon emission, such as might be designed by the method of FIG. 7.

FIG. 8 shows a design for a semiconductor device 800, according to various exemplary embodiments of the present invention. The principles and operations of device 800 are similar to the principles and operations of device 300 (see FIG. 3). The difference in that device 800 further comprises an optical cavity 806, which provides three-dimensional confinement to the emitted photons 212 and 214 hence select particular frequencies $\omega_1$ and $\omega_2$ thereto. Thus, device 800 emits photons at predetermined frequencies. Optical cavity 806 can be any cavity known in the art, such as the optical cavity disclosed in Hayat et al Phys. Rev. B supra. In the representative example illustrated in FIG. 8, optical cavity 806 is realized as a plurality of layers 804 which provide vertical confinement (along z direction) and a two-dimensional photonic crystal 808 which provides horizontal confinement (in the x and y directions). Layers 804 can be realized, for example, as Bragg reflectors above and below quantum wells 302. Other types of optical cavities are not excluded from the scope of the present invention.

Figure 9:
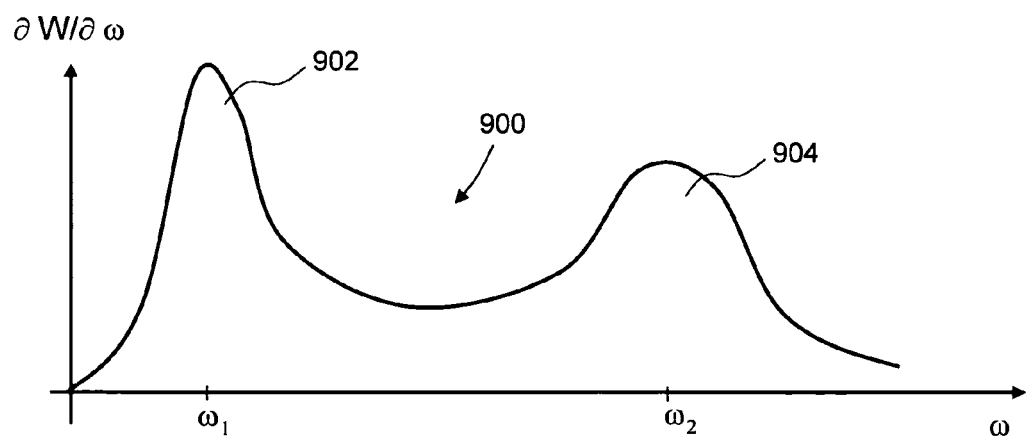
FIG. 9 schematically shows a two photon emission spectrum, such as might be calculated in the method of FIG. 7.

FIG. 9 schematically shows a two photon emission spectrum 900, such as might be calculated from Eqs. (2) and (3) of Hayat et al. There is a peak 902 at a frequency of $\omega_1$, whose height and width depend on the dephasing factor $\Gamma$. If $\Gamma$ were zero, the emission spectrum would diverge at zero frequency. There is also a peak 904 at a frequency of $\omega_2$, which is typically near $E_g/\hbar$ where $E_g$ is the minimum energy gap between the conduction and valence band, i.e. the gap at zero crystal momentum. The width and height of peak 904 also depend on the dephasing factor Γ. The width and height of the peaks may also depend on the temperature, since there will be a spread in the effective gap energy due to the spread electron momentum associated with the thermal spread in electron energy, in the valence and conduction bands.

The two-photon emission device of the present embodiments has many potential applications.

For example, in an aspect of some embodiments of the present invention the two-photon emission device is used for two-photon microscopy, two-photon spectroscopy and/or two-photon imaging. In these embodiments the device emits two photons in the direction of a sample to induce two-photon absorption in the sample. Two-photon absorption is a process in which two distinct photons are absorbed by an ion or molecule, causing excitation from the ground state to a higher energy state to be achieved. The ion or molecule remains in the upper excited state for a short time, commonly known as the excited state lifetime, after which it relaxes back to the ground state, giving up the excess energy in the form of photons.

The use of the device of the present embodiments for microscopy and/or spectroscopy is advantageous because it allows a wider energy gap hence reduces or eliminates background photons emitted by other mechanism (e.g., infrared photons or photon emitted by thermal excitations). Thus, the two-photon emission device of the present embodiments increases signal to noise ratio.

When considering fluorescence, an important figure of merit is the quantum efficiency, defined to be the visible fluorescence intensity divided by the total input intensity. For display or spectroscopic applications based on two-photon induced fluorescence, the use of the two-photon device of the present embodiments facilitates dominance of radiative relaxation over non-radiative relaxation (phonons) hence increases the quantum efficiency.

Figure 10A:
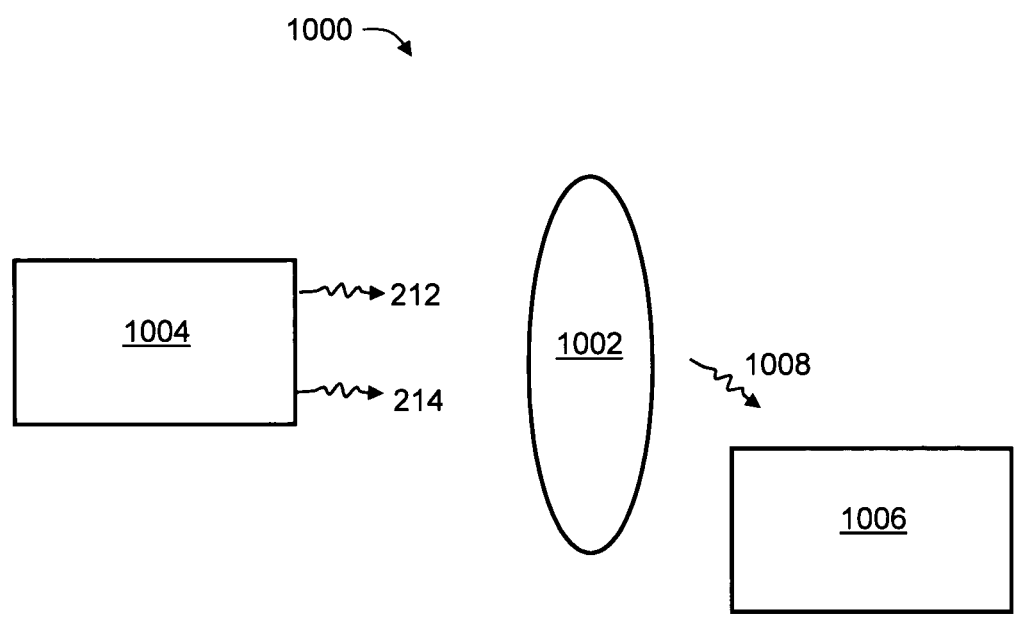
FIGS. 10a-c are schematic illustrations of a system for analyzing a material by two photon emission, according to various exemplary embodiments of the present invention.
Figure 10B:
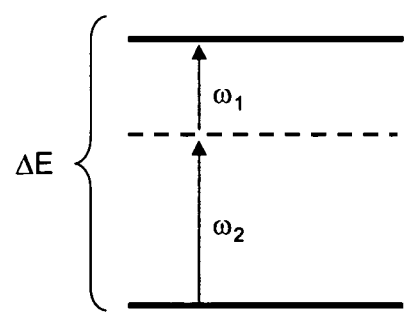

FIGS. 10a-b are schematic illustrations of a system 1000 for analyzing a target material 1002 by two photon absorption. System 1000 can be used for spectroscopy, microscopy and/or imaging of target material 1002. For example, when target material 1002 contains a fluorophore therein, system 1000 can be used for fluorescence spectroscopy. Representative examples of fluorophores suitable for the present embodiments include fluorophores which exhibit two-photon absorption cross-sections, such as the compositions described in U.S. Pat. No. 5,912,257, the contents of which are hereby incorporated by reference. Also contemplated are fluorophores which are normally excitable by a single short wavelength photon (e.g., ultraviolet photon). In this embodiment, the two-photon emission device emits two long wavelength photons (e.g., infrared photons) which can be simultaneously absorbed by such fluorophores.

System 1000 comprises a two-photon emission device 1004 which emits two photons 212 and 214 in the direction of material 1002 to induce two-photon absorption therein. Device 1004 can be any of the aforementioned two-photon emission devices described above. Preferably, device 1004 emits photons at predetermined frequencies at frequencies $\omega_1$ and $\omega_2$ as further detailed hereinabove. The characteristic energy diagram is illustrated in FIG. 10b showing an energy gap $\Delta E = h(\omega_1 + \omega_2)/2\pi$. Thus photons generate excitation across $\Delta E$. The value of the frequencies $\omega_1$ and $\omega_2$, is preferably selected such that $\Delta E$ is higher than the average energy of thermal and other background (e.g., infrared) photons.

Once the material returns to its ground state, it emits radiation 1008 which can be detected by a detector 1006, as known in the art. System 1000 can employ any of the components of known systems for the analysis or imaging via two-photon absorption, see, e.g., U.S. Pat. Nos. 5,034,613, 6,020,591, 5,957,960, 6,267,913, 5,684,621, the contents of which are hereby incorporated by reference.

Figure 10C:
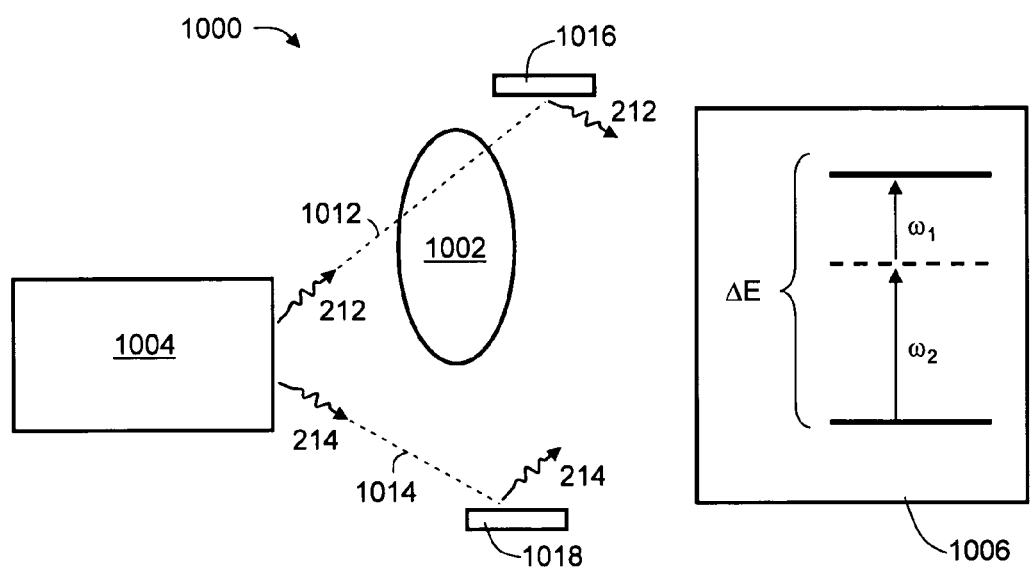

Reference is now made to FIG. 10c, which is a schematic illustration of system 1000 in an embodiment in which the detection is based on two-photon absorption. In this embodiment, the optical path 1012 of photon 212 can be arranged to pass through material 1002 and the optical path 1014 of photon 214 can be arranged to bypass material 1002. Both optical paths 1012 and 1014 terminate as detector 1006. Thus, photon 212 can serve as a signal photon and photon 214 can serve as an idler photon.

The wavelength of photon 212 is preferably selected to allow photon 212 to excite the molecules in material 1002. For example, the wavelength of photon 212 can be selected to match the vibrational or rotational resonances of the molecules in the material. In biological materials, such resonances are typically in the mid infrared or far infrared. For example, most of the absorption spectra of organic compounds are generated by the vibrational overtones or the combination bands of the fundamentals of O—H, C—H, N—H, and C—C transitions. Thus, for biological materials, photon 212 can be a mid infrared photon or a far infrared photon. Also contemplated are embodiments in which photon 212 is a near infrared photon which can be suitable for molecular overtone (harmonic) and combination vibrations. The use of other wavelengths (e.g., visible photons) is not excluded from the scope of the present invention.

Optical paths 1012 and 1014 can be established via an arrangement of optical elements 1016 and 1018 such as, but not limited to, mirrors, lenses, prisms, gratings, holographic elements, graded-index optical elements, optical fibers, or other similar beam-directing mechanisms.

When signal photon 212 passes through the material, it can be either absorbed by the material giving rise to a resonance in one of the molecules or continue to propagate therethrough, with or without experiencing scattering events. If signal photon 212 is not absorbed it can continue along path 1012 to detector 1006. Preferably optical paths 1012 and 1014 are of the same lengths such that when signal photon 212 successfully arrives at detector 1006 it arrives simultaneously with idler photon 214.

Detector 1006 is preferably characterized by a detection threshold which equals the sum of energies of photons 212 and 214. This can be achieved using a semiconductor detector having a sufficiently wide bandgap to allow two-photon absorption. For example, detector 1006 can be an Si detector.

Having a wide bandgap, detector 1006 does not provide a detection signal when only idler photon 214 arrives. Additionally, the wide bandgap prevents or reduces triggering of device 1006 by noise, such as infrared background photons because the energy of such photons is lower than the detection threshold and further because triggering caused by simultaneous arrival of two background photons is extremely rare due to the random nature of the background photons.

Thus, detector 1006 provides indication of simultaneous arrival of the signal-idler photons pair, in a substantially noise-free manner. Such indication can provide information regarding material 1002 by means of transmission spectroscopy because the resonances appear as dips in the spectrum on the detector output. System 1000 can also operate according to similar principles in reflectance spectroscopy.

In an aspect of some embodiments of the present invention the two-photon emission device is used for communication applications. Since the device of the present embodiments typically emits two-photons simultaneously, the existence of one photon is an indication of the existence of another photon. Thus, a communication system incorporating the device of the present embodiments can use one photon as a signal and the other photon as an idler. More specifically, such communication system can transmit one photon to a distant location and use the other photon as an indication that a transmission is being made.

Figure 11:
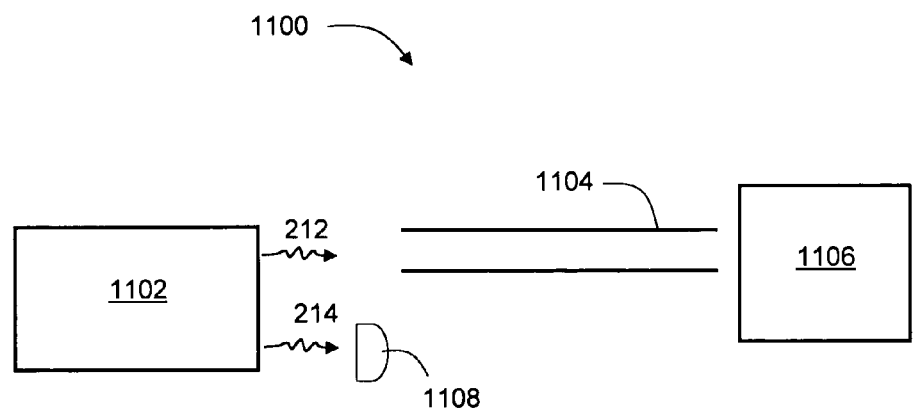
FIG. 11 is a schematic illustration of a communication system according to various exemplary embodiments of the present invention.

FIG. 11 is a schematic illustration of a communication system 1100 according to various exemplary embodiments of the present invention. System 1100 comprises a two-photon emission device 1102 which emits two photons 212 and 214. Device 1102 can be any of the aforementioned two-photon emission devices described above. Preferably, device 1102 emits photons at predetermined frequencies at frequencies $\omega_1$ and $\omega_2$ as further detailed hereinabove. One photon (photon 212 in the present example) serves as a signal as is being transmitted over a communication channel 1104 such as an optical fiber or free air, while the other photon (photon 214 in the present example) serves as an idler and being detected by a detector for indicating that the signal has been transmitted.

Such communication system can be used for quantum cryptography and quantum teleportation.

Quantum cryptography provides security by means of physical phenomenon by the uncertainty principle of Heisenberg in the quantum theory. According to the uncertainty principle, the state of quantum will be changed once it is observed, wiretapping (observation) of communication will be inevitably detectable. This allows to take measures against the wiretapping, such as shutting down the communication upon the detection of wiretapping. Thus, quantum cryptography makes undetectable wiretapping impossible physically. Moreover, the uncertainty principle explains that it is impossible to replicate particles.

Quantum teleportation is a technique to transfer quantum information ("qubits") from one place where the photons exist to another place.

A qubit is a quantum bit, the counterpart in quantum communication and computing to the binary digit or bit of classical communication and computing. Just as a bit is the basic unit of information in a classical signal, a qubit is the basic unit of information in a quantum signal. A qubit is conventionally a system having two degenerate (e.g., of equal energy) quantum states, wherein the quantum state of the qubit can be in a superposition of the two degenerate states. The two degenerate states are also referred to as basis states, and typically denoted |0> and |1>. The qubit can be in any superposition of these two degenerate states, making it fundamentally different from an ordinary digital bit.

Quantum teleportation can be used to transmit quantum information in the absence of a quantum communications channel linking the sender of the quantum information to the recipient of the quantum information. Suppose, for example, that a sender, Bob, receives a qubit $\alpha|0>+\beta|1>$ where and $\alpha$ and $\beta$ are parameters on a unit circle. Bob needs to transmit to a receiver, Alice, but he does not know the value of the parameters and he can only transmit classical information over to Alice. According to the laws of quantum teleportation Bob can transmit information over a classical channel, provided Bob and Alice agree in advance to share a Bell state generated by an entangled state source. Such entangled state source can be the two-photon emission device of the present embodiments.

Thus, the device of the present embodiments can emit photons in a quantum entangled state hence be used in quantum cryptography and quantum teleportation.

In an aspect of some embodiments of the present invention the two-photon emission device is used as a component in a quantum computer.

Quantum computing generally involves initializing the states of several entangled qubits, allowing these states to evolve, and reading out the states of the qubits after the evolution. N entangled qubits can define an initial state that is a combination of $2^N$ classical states. This initial state undergoes an evolution, governed by the interactions that the qubits have among themselves and with external influences, providing quantum mechanical operations that have no analogy with classical computing. The evolution of the states of N qubits defines a calculation or, in effect, $2^N$ simultaneous classical calculations (e.g., conventional calculations as in those performed using a conventional computer). Reading out the states of the qubits after evolution completely determines the results of the calculations. For example, when there are two entangled qubits, $2^2=4$ simultaneous classical calculations can be performed. Taken together, quantum superposition and entanglement create an enormously enhanced computing power. Where a 2-bit register in an ordinary computer can store only one of four binary configurations (00, 01, 10, or 11) at any given time, a 2-qubit register in a quantum computer can store all four numbers simultaneously, because each qubit represents two values. If more qubits are entangled, the increased capacity is expanded exponentially.

Figure 12:
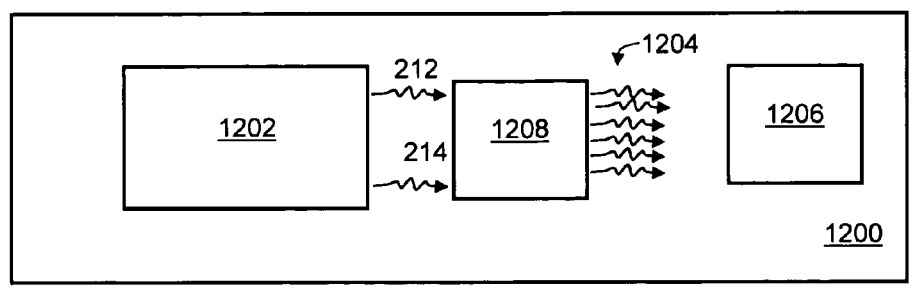
FIG. 12 is a schematic illustration of a quantum computer system according to various exemplary embodiments of the present invention.

FIG. 12 is a schematic illustration of a quantum computer system 1200 according to various exemplary embodiments of the present invention. System 1200 comprises a two-photon emission device 1202 which emits two photons 212 and 214, as describe above. In this embodiment, photons 212 and 214 are in entangled state. Device 1202 can be any of the aforementioned two-photon emission devices. System 1200 further comprises a calculation unit 1206 which uses the photons as entangled qubits and perform calculations as known in the art (see, e.g., U.S. Pat. No. 6,605,822, the contents of which are hereby incorporated by reference). In various exemplary embodiments of the invention system 1200 comprises an optical mechanism 1208 for the generation of more than two entangled photons. For example, such mechanism can receives photons 212 and 214 emitted by device 1202, generate by reflection, refraction or diffraction two or more photons from each photon, so as to produce a plurality of entangled photons 1204.

In an aspect of some embodiments of the present invention the two-photon emission device is used as an optical amplifier. In these embodiments, the energy spectrum emitted by the two-photon is sufficiently broad as further detailed hereinabove.

The use of the two-photon emission device of the present embodiments as an optical amplifier is advantageous because the gain in two-photon amplifier, in contrast to conventional single photon lasers, is nonlinear, depending on the amplitude of the light wave. Such two-photon amplifier can also be used for pulse generation. Since the length of the pulse is a decreasing function of the gain bandwidth of the amplifier, the broad spectrum of the two-photon device of the present embodiments facilitate generation of very short pulses.

Figure 13:
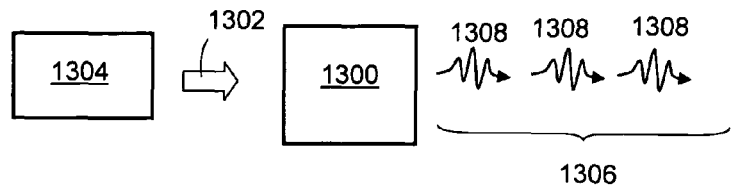
FIG. 13 is a schematic illustration of an optical amplifier, according to various exemplary embodiments of the present invention.

FIG. 13 is a schematic illustration of an optical amplifier 1300, according to various exemplary embodiments of the present invention. Amplifier 1300 receives input light 1302 from an input light source 1304, amplifies the light by two photon emission and produces an amplified light 1306, typically in the form of short pulses 1308. Amplifier 1300 comprises a two-photon emission device which can be any of the two-photon emission devices described above.

Figure 14:
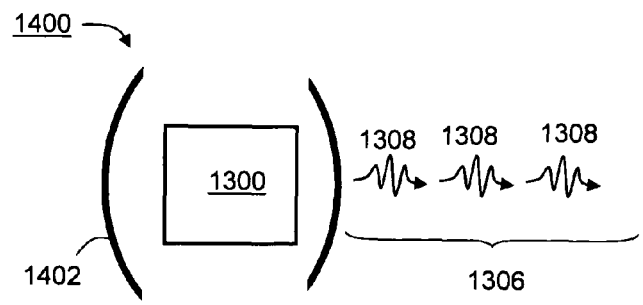
FIG. 14 is a schematic illustration of a two-photon laser device, according to various exemplary embodiments of the present invention.

FIG. 14 is a schematic illustration of a two-photon laser device 1400, according to various exemplary embodiments of the present invention. Laser device 1400 is similar to optical amplifier 1300 except that it further includes an optical cavity 1402 for providing optical feedback.

Optical amplifier 1300 and/or laser 1400 typically operate at low input peak powers. In various exemplary embodiments of the invention amplifier 1300 and/or laser 1400 operates at input peak power of less than 1000 W, more preferably less than 500 W, more preferably less than 250 W, more preferably less than 100 W, more preferably less than 50 W, more preferably less than 10 W, more preferably less than 1 W.

Figure 15:
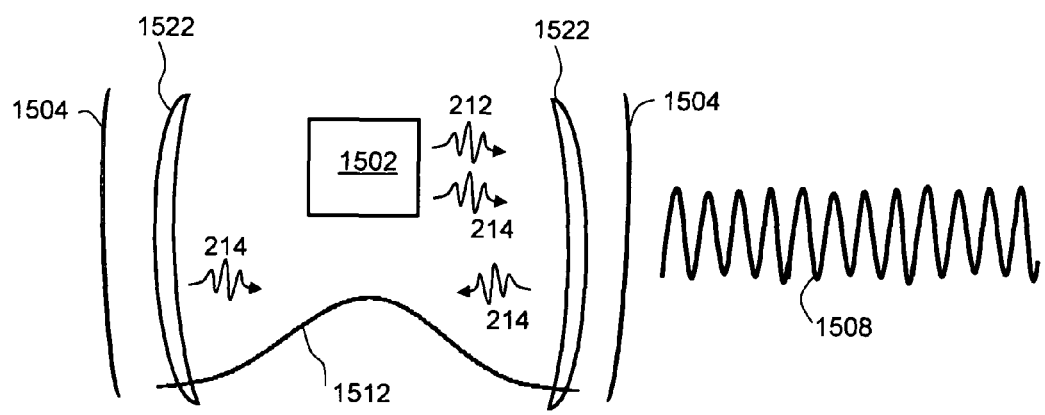
FIG. 15 is a schematic illustration of a continuous wave (CW) two-photon laser device, according to various exemplary embodiments of the present invention.

FIG. 15 is a schematic illustration of a continuous wave (CW) two-photon laser device 1500, according to various exemplary embodiments of the present invention. Device 1500 comprises a two-photon emission device 1502 which emits two photons 212 and 214, referred to hereinunder as a signal photon and an idler photon respectively. In this embodiment, the photons are preferably non-degenerate with different wavelengths. Device 1502 can be any of the aforementioned two-photon emission devices.

The non-degenerate state of the photons (different wavelengths) allows the employment of a two-resonance cavity 1522 which provides a first resonance for photon 214 and a second resonance for photon 212. In various exemplary embodiments of the invention the first resonance is of higher quality factor than the second resonance, such as to provide large number $N_i$ of photons at the wavelength of idler photon 214 and smaller number of photons $N_s$ at the wavelength of signal photon 212. The quality factors of the resonances is preferably selected such that the multiplication $N_i \times N_s$ is sufficiently high to establish lasing oscillation condition at sufficiently low pumping power. Thus, in these embodiments the lasing oscillation condition is established predominantly due to photons at the wavelength of idler photon 214. The idler optical mode is illustrated at 1512.

Since the resonance quality factor of the idler photon 214 is high, the optical output power of device 1500 for the wavelength of photon 214 is relatively low. On the other hand, since the resonance quality factor of photon 212 is low, the optical power of device 1500 for the wavelength of photon 212 is relatively high. Thus, device 1500 produces CW laser radiation 1508 at the wavelength of signal photon 212. The advantage of using high resonance quality factor for the idler photon and low resonance quality factor for the signal photon is that it facilitates high output power while maintaining low lasing threshold.

The resonances of cavity 1522 are optionally tunable so as to allow selection of the CW wavelength outputted from device 1500. This can be done, for example, using external optical elements 1504 which can be made rotatable or slideable. external optical elements 1504 can be for example, mirrors, gratings and the like. Optionally the tuning can be done by integrated tunable Bragg reflectors controlled by voltage, current or temperature.

Coherent stimulated non-degenerate two-photon emission from atomic vapors was previously reported by B. Nikolaus, D. Z. Zhang, and P. E. Toschek, Phys. Rev. Lett. 47, 171 (1981), the contents of which are hereby incorporated by reference.

As used herein the term "about" refers to ±10%.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. For example, any of the limitations on operating temperature, emission power, emission power per area, broadness of emission spectrum, range of photon energy, and nature of the emission process (for example two photon emission) and other device parameters described for any embodiment of the invention may be combined in a single embodiment of the invention As used herein, the terms "have", "include" and "comprise" or their conjugates mean "including but not limited to."

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A two photon emission system comprising:
  a) a two-resonance semiconductor photonic microcavity, comprising a heterostructure, and characterized by a density of photon states; and
  b) an electric power source comprising electrical leads and contacts to provide electric current to the semiconductor photonic microcavity, configured for pumping electrons into a conduction band of the semiconductor with a predetermined energy distribution;
  wherein a combination of said density of photon states and said energy distribution is selected, such that, when electrons are pumped into the conduction band by the electric power source non-thermal quantum-entangled photon pairs are generated, wherein the characteristic spectrum of the quantum-entangled photon pairs is sufficiently broad so that no more than half the power emitted within said spectrum is emitted within any energy range within said spectrum that is narrower than 15% of the mean photon energy within said spectrum, wherein said semiconductor photonic microcavity comprises a plurality of layers which provide vertical confinement and preferentially select from said spectrum a first frequency and a second frequency to effect surface emission of quantum-entangled photon pairs at said first and said second frequencies, and at a power per area of at least 1 W/m$^2$.

2. A system according to claim 1, wherein the two photon emission power per area is at least 3 W/m$^2$.

3. A system according to claim 2, wherein the two photon emission power per area is at least 10 W/m$^2$.

4. A system according to claim 3, wherein the two photon emission power per area is at least 30 W/m$^2$.

5. A system according to claim 1, wherein the device is capable of producing a two photon emission power of at least 1 nW.

6. A system according to claim 5, wherein the device is capable of producing a two photon emission power of at least 3 nW.

7. A system according to claim 6, wherein the device is capable of producing a two photon emission power of at least 10 nW.

8. A system according to claim 7, wherein the device is capable of producing a two photon emission power of at least 30 nW.

9. A system according to claim 1, wherein the device is capable of producing a two photon emission power of at least 1 W/m$^2$ at at least one temperature is greater than 50 K.

10. A system according to claim 9, wherein the at least one temperature is greater than 100 K.

11. A system according to claim 10, wherein the at least one temperature is greater than 200 K.

12. A system according to claim 1, wherein the heterostructure comprises a quantum well.

13. A system according to claim 1, with energy efficiency greater than $1 \times 10^{-9}$.

14. A system according to claim 1, comprising an anti-reflection coating of sufficiently low reflectivity so that the lasing threshold is greater than $2 \times 10^8$ A/m$^2$.

15. A system for analyzing a target material, comprising: a) a two photon emission system according to claim 1, tuned to emit a photon pair comprising first and second photons at predetermined first and second frequencies;
b) a detector characterized by a detection threshold which provides a detection signal if the first and second photons arrive at the detector simultaneously, but not if only the second photon arrives at the detector;
c) an optical path arranged to pass the first photon through the target material, and an optical path arranged so that the second photon bypasses the target material, both paths terminating at the detector.

16. A system for imaging a material, the system comprising:
a) a two photon emission system according to claim 1, which emits a pair photons toward the material, with an energy to induce two photon absorption in the material, raising it to an excited state; and
b) a detector which detects radiation emitted by the material when it returns to a ground state.

17. A communication system comprising:
a) a two photon emission system according to claim 1, tuned to emit a photon pair comprising first and second photons at predetermined first and second frequencies;
b) a communication channel configured to transmit the first photons as a signal; and
c) a detector configured to detect the second photons, to indicate that the signal has been transmitted.

18. A quantum teleportation system comprising a communication system according to claim 17, wherein the two photon emission system is configured to emit the photon pairs with the first and second photons in an entangled Bell state, and the communication channel is a quantum communication channel for sharing the entangled Bell state between two users, the quantum teleportation system also including a classical communication channel between the two users, for teleporting quantum states between the users, using the entangled Bell state, after sharing the entangled Bell state.

19. A quantum cryptography system comprising a communication system according to claim 17, wherein the two photon emission system is configured to emit the photon pairs with the first and second photons in an entangled state, and the detector is configured to detect wiretapping of the communications channel by detecting changes in the state of the second photons indicating the wiretapping.

20. A quantum computer comprising:
a) a two photon emission system according to claim 1, configured to emit a pair of photons in a quantum entangled state of two photons;
b) an optical mechanism configured for generating a quantum entangled state of more than two photons from the quantum entangled state of two photons; and
c) a calculation unit configured for using the quantum entangled state of more than two photons as entangled qubits for performing a calculation.

21. A two photon emission system according to claim 1, wherein no more than half the two photon emission power emitted within said spectrum is emitted within any energy range of within said spectrum that is narrower than 30% of the mean photon energy within said spectrum.

22. A two photon emission system according to claim 1, wherein no more than half the two photon emission power emitted within the range of photon energies of two photon emission is emitted within any sub-range of the range that is narrower than 0.3 eV.

23. The system of claim 1, serving as an optical amplifier.

24. The system of claim 1, serving as laser device, wherein the photonic microcavity is of sufficiently high quality factor, and the electric power source supplies enough pumping power to the semiconductor heterostructure, to meet a two-photon lasing threshold.

25. A system for analyzing a target material, comprising:
the system according to claim 1; and
a photon detector;
wherein said photon pairs comprise a pair which includes a signal photon and an idler photon, and said photon detector is characterized by a detection threshold which equals the sum of energies of said signal photon and said idler photon; and
wherein an optical path for said signal photon is defined from said semiconductor device through said target material to said detector, and an optical path for said idler photon is defined from said semiconductor device to said detector while bypassing said target material.

26. A two photon emission system according to claim 1, which is capable of producing at least 1 W/m² two photon emission power per area, when operating at at least one temperature greater than 20 K.

27. A method of producing light, comprising:
injecting sufficient current into a semiconductor device to generate a continuous spectrum of quantum-entangled photon pairs at power per area of at least 1 W/m², while maintaining the temperature of the semiconductor device at a temperature within ±10% of 300 K, wherein said continuous spectrum is sufficiently broad so that no more than half the power emitted within said continuous spectrum is emitted within any energy range within said continuous spectrum that is narrower than 15% of the mean photon energy within said continuous spectrum, and using a two-resonance cavity to preferentially select from said continuous spectrum a first frequency and a second frequency, and to effect emission of quantum-entangled photon pairs at said first and said second frequency and at power per area of at least 1 W/m².

28. The system of claim 1, wherein said two-resonance semiconductor photonic microcavity is a vertical two-resonance semiconductor photonic surface emitting microcavity.

* * * * *